United States Patent
Province

(10) Patent No.: US 7,136,700 B1
(45) Date of Patent: Nov. 14, 2006

(54) SYSTEM AND METHOD FOR DELIVERING POST-ATRIAL ARRHYTHMIA THERAPY

(75) Inventor: Rose A. Province, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 563 days.

(21) Appl. No.: 10/453,439

(22) Filed: Jun. 2, 2003

(51) Int. Cl.
*A61N 1/39* (2006.01)

(52) U.S. Cl. .............................. 607/4; 607/14; 607/5

(58) Field of Classification Search ................. 607/14, 607/4, 15, 5, 9
See application file for complete search history.

(56) References Cited

U.S. PATENT DOCUMENTS

| | | | | |
|---|---|---|---|---|
| 5,007,422 A | * | 4/1991 | Pless et al. ..................... | 607/4 |
| 5,265,600 A | | 11/1993 | Adams et al. ................. | 607/4 |
| 5,527,345 A | | 6/1996 | Infinger .......................... | 607/4 |
| 5,584,864 A | * | 12/1996 | White ............................ | 607/5 |
| 5,645,569 A | | 7/1997 | Ayers ............................. | 607/4 |
| 5,676,687 A | | 10/1997 | Ayers ............................. | 607/4 |
| 5,713,929 A | | 2/1998 | Hess et al. ..................... | 607/14 |
| 5,865,838 A | * | 2/1999 | Obel et al. ..................... | 607/5 |
| 5,978,709 A | | 11/1999 | Begemann et al. ........... | 607/14 |
| 6,058,328 A | | 5/2000 | Levine et al. ................. | 607/14 |
| 6,178,351 B1 | * | 1/2001 | Mower ........................... | 607/5 |
| 6,272,380 B1 | * | 8/2001 | Warman et al. ............... | 607/5 |
| 6,311,089 B1 | * | 10/2001 | Mann et al. ................... | 607/30 |
| 6,377,852 B1 | * | 4/2002 | Bornzin et al. ............... | 607/9 |

* cited by examiner

*Primary Examiner*—George R. Evanisko
(74) *Attorney, Agent, or Firm*—Steven M. Mitchell

(57) ABSTRACT

A system and method for applying atrial therapy to a human heart using a defibrillator includes detecting an atrial arrhythmia and delivering electrical energy to at least one atrium in response to a detected atrial arrhythmia. A first atrial activation is detected after delivering the electrical energy, occurrence of a detected first atrial activation defining a first moment. Finally, a first pacing pulse is delivered to a number of locations within the atria when the first atrial activation is detected. The first pacing pulse is delivered at a second moment substantially synchronous with the first moment.

65 Claims, 6 Drawing Sheets

SYSTEM AND METHOD FOR DELIVERING POST-ATRIAL ARRHYTHMIA THERAPY

BACKGROUND OF THE INVENTION

1. Field of the Invention

The present invention relates generally to cardiac pacing therapy. More particularly, the present invention relates to a system and method for providing atrial pacing in order to prevent the immediate reentry into fibrillation following the application of an atrial arrhythmia termination therapy.

2. Related Art

Atrial fibrillation is a common cardiac arrhythmia in which small areas of atrial tissue repeatedly depolarize in a disorderly fashion when compared to neighboring areas of atrial tissue. Although it is not normally a life-threatening arrhythmia, it is well-known that atrial arrhythmias lead to dizziness resulting from reduced cardiac output, palpitations of the heart, and even stroke. Atrial fibrillation may be corrected by an external defibrillator configured to apply electrical energy to the heart through the skin of a patient, or through use of an implantable device applying electrical energy to the heart based upon detected R waves produced by the heart. Cardioversion, for example, is a conventional type of post-atrial arrhythmia termination therapy used to treat atrial fibrillation.

A problem with the conventional treatment of atrial fibrillation, also known as atrial therapy, is that the treatments are often followed by an early return to atrial fibrillation (ERAF) after a few cardiac sinus intervals. ERAF reduces the success rate of the pacing therapy and forces repeated and higher-amplitude shocks resulting in additional patient discomfort. The cause of ERAF is not completely understood. It is hypothesized, however, that it might be related to a time-delay in the remodeling of the effective refractive period (ERP) and conduction velocity of the atria. Other hypotheses suggest that it could also be related to a level of dispersion of ERP that exists during atrial fibrillation that might still be present within the first few minutes following cardioversion.

A number of systems have been presented in an attempt to treat various effects of atrial fibrillation. For example, U.S. Pat. No. 5,527,345 issued to Infinger discloses an atrial defibrillator for applying cardioverting electrical energy to the atria of a human heart in need of cardioversion and thereafter pacing the heart in a demand mode. In particular, Infinger relates to the pacing of the ventricles at a base rate following cardioversion to treat sinus node dysfunction, which can lead to dizziness or possible ventricular arrhythmia.

Similarly, U.S. Pat. No. 5,265,600 issued to Adams et al, discloses an implantable atrial defibrillator for applying cardioverting electrical energy to the atria of a human heart in need of atrial therapy and thereafter gradually returning the cardiac rate of the heart to a normal cardiac rate. Although Adams et al. and Infinger address treatment of various aspects of atrial fibrillation, neither discloses a method or technique for treating reinitiation of atrial fibrillation.

Next, U.S. Pat. No. 5,645,569 issued to Ayers, (the '569 patent) discloses an atrial cardioverter/defibrillator and method, wherein after each application of atrial cardioversion therapy, the atria are paced to prevent spontaneous reversion from a normal sinus rhythm back to atrial defibrillation.

Finally, U.S. Pat. No. 5,676,687, issued to Ayers (the '687 patent) discloses an atrial cardioverter defibrillator and method, wherein the atria are paced from a relatively high rate to a gradually derived normal or bradycardia rate to prevent spontaneous reversion from a normal sinus rhythm back to atrial fibrillation. The '687 patent and the '569 patent both address pacing following cardioversion to prevent arrhythmia reinitiation. The '569 patent, however, primarily addresses current clinical pacing modes such as atrial pacing (AAI) and dual-chamber pacing (DDD).

AAI atrial pacing is inhibited by sensing in the atria and DDD pacing is inhibited by sensing in the atria or ventricle. The '687 patent discloses a technique by which the atria are paced in a demand mode at a rate greater than the brady rate, followed by a gradual decrease to a bradycardia rate. Both the '569 patent and the '687 patent allow for an initial unsynchronized pacing pulse that may be conducive to initiating an arrhythmia.

The '569 and '687 patents discuss pacing either in the right atria, the left atria, or pacing between the atria. Both patents also call for pacing termination at the end of a fixed time interval or a certain number of sequential sense events. Conventional techniques have not been shown to be particularly effective at preventing reinitiation of atrial fibrillation following cardioversion therapy.

What is needed, therefore, is a system and method for preventing ERAF following the application of post-atrial arrhythmia therapy.

SUMMARY OF THE INVENTION

Consistent with the principles of the present invention as embodied and broadly described herein, an exemplary technique includes a method of applying atrial pacing therapy to a human heart using, for example, an implantable cardioverter defibrillator (ICD). The method comprises detecting an atrial arrhythmia and delivering therapeutic electrical energy to at least one atria in response to a detected atrial arrhythmia. The method also includes detecting a first atrial activation after delivering the therapeutic electrical energy, the occurrence of a detected first atrial activation defining a first moment. A first pacing pulse is delivered to a number of locations within the atria when the first atrial activation is detected, wherein the first pacing pulse is delivered at a second moment. The first and second moments are substantially synchronous.

An alternative embodiment of the present invention includes a method of applying therapeutic energy to a human heart using a stimulation device comprising detecting an atrial arrhythmia and delivering therapeutic electrical energy to at least one atrium in response to a detected atrial arrhythmia. The method includes detecting a first atrial activation within a number of sense channels after delivering the therapeutic electrical energy, occurrence of a detected first atrial activation defining a first moment. Next, a first determination is performed of whether the number of sense channels is in a vulnerable state. If none of the sense channels are determined to be in a vulnerable state based upon the first determination, a first pacing pulse is delivered to a number of locations within the atria at a second moment. The first and second moments are substantially synchronous.

Features and advantages of the present invention include the delivery of pacing stimuli at multiple sites in the atria immediately following delivery of atrial therapy and synchronous with a first activation in order to prevent ERAF. Therefore, the present invention is sensitive to the inherent activation time and repolarization time within the atria, causing a faster total activation time of associated cardiac tissue. This technique reduces the chance of ERAF that might be caused by dispersion of repolarization. This technique also avoids the danger of delivering a stimulus during the vulnerable period of the heart, which ultimately decreases the risk of returning to atrial fibrillation. Multiple site stimulation, as accomplished in the present invention, has also been shown to reduce the total activation time of the heart.

Another advantage in the multi-site pacing technique of the present invention is the ability to decrease the delay in the activation of the atria so that the chance of a reentry wavefront or a focal activation taking over will be minimized. If ERAF is reduced by therapy, then the atrial defibrillation threshold (ADFT) will also be lowered due to a greater atrial pacing therapy success rate at defibrillation levels close to the ADFT. The technique of the present invention will not produce additional discomfort to the patient, and due to the smart timing, the risk of inducing atrial fibrillation with the pacing pulses is minimal. Finally, the present invention can be implemented using leads currently available in conventional dual-chamber defibrillation devices.

Further embodiments, features, and advantages of the present invention, as well as the structure and operation of the various embodiments of the present invention, are described in detail below with reference to the accompanying drawings.

BRIEF DESCRIPTION OF THE DRAWINGS

The accompanying drawings, which are incorporated in and constitute part of the specification, illustrate an embodiment of the invention and, together with the description, explain the purpose, advantages, and principles of the invention.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

Figure 1A:
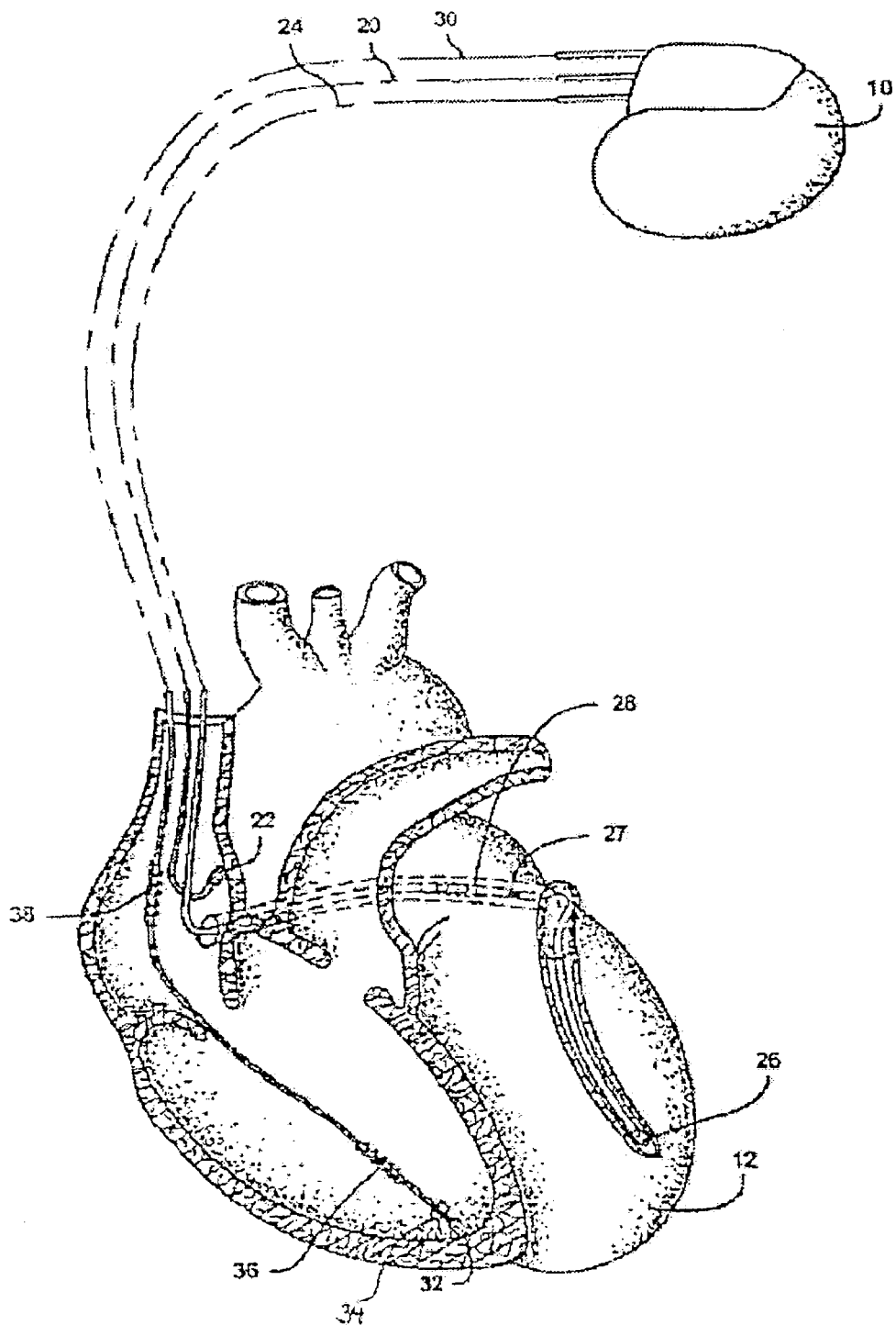
FIG. 1A is a simplified diagram illustrating an implantable stimulation device in electrical communication with at least three leads implanted into a patient's heart for delivering multi-chamber stimulation and shock therapy.
Figure 1B:
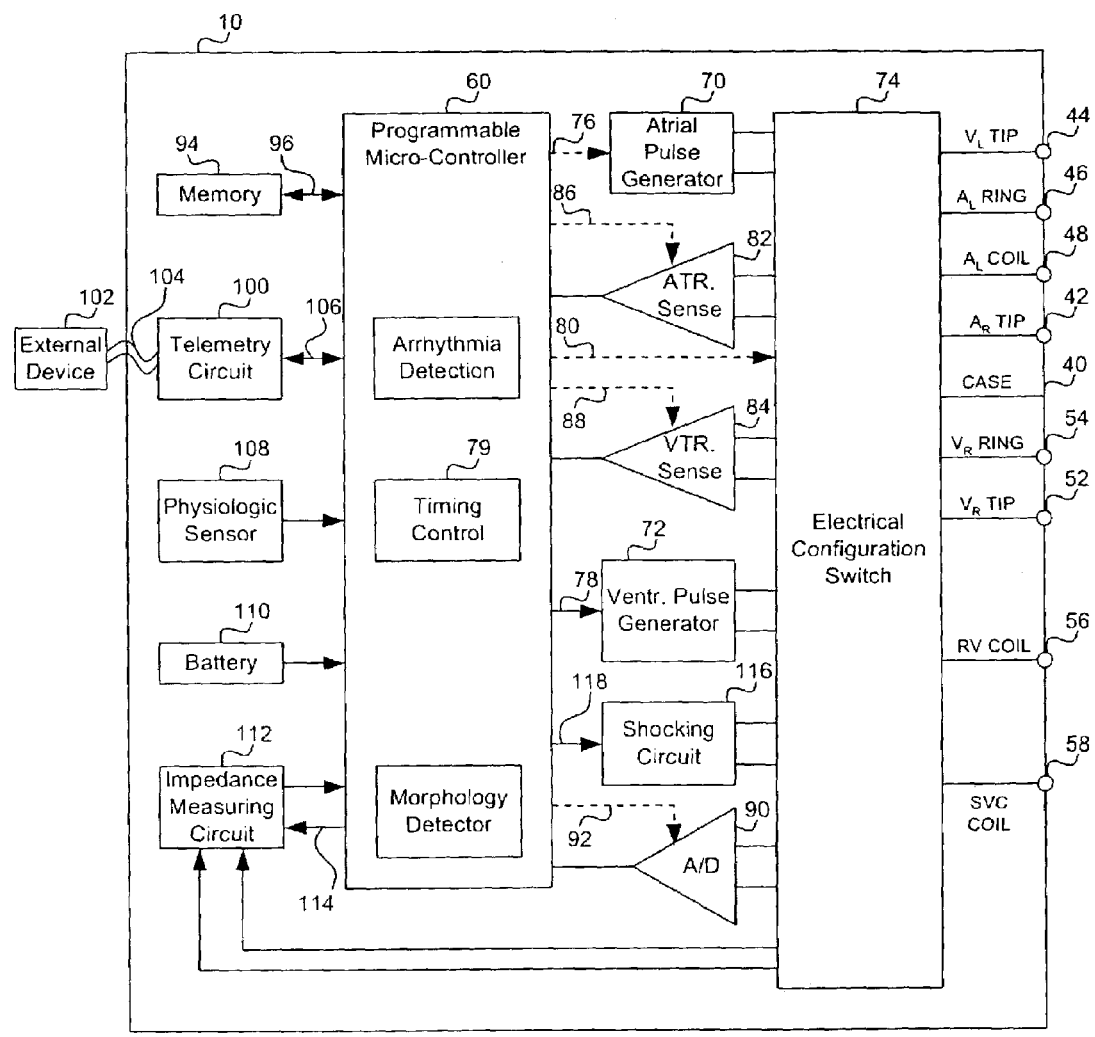
FIG. 1B is a functional block diagram of a multi-chamber implantable stimulation device illustrating the basic elements of a stimulation device which can provide cardioversion, defibrillation and pacing stimulation in four chambers of the heart.

It would be apparent to one of skill in the art that the present invention, as described below, may be implemented in many different embodiments of hardware, software, firmware, and/or the entities illustrated in the figures. Any actual software code with specialized control hardware to implement the present invention is not limiting of the present invention. Thus, the operation and behavior of the present invention will be described with the understanding that modifications and variations of the embodiments are possible, given the level of detail presented herein. Before describing the invention in detail, it is helpful to describe an example environment in which the invention may be implemented. The present invention is particularly useful in the environment of an ICD. FIGS. 1A 1B and illustrate such an environment.

As shown in FIG. 1A, there is an exemplary stimulation device 10 (also referred to as a pacing device, or a pacing apparatus) in electrical communication with a patient's heart 12 by way of three leads, 20, 24 and 30, suitable for delivering multi-chamber stimulation and pacing therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

As illustrated in FIG. 1B, a simplified block diagram is shown of the multi-chamber stimulation device 10, which is capable of treating both fast and slow arrhythmias with stimulation therapy, including cardioversion, defibrillation, and pacing stimulation. While a particular multi-chamber device is shown, its showing is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 1B, is often referred to as the "can," "case" or "case electrode" and may be programmably selected to act as the return electrode for all "unipolar" modes. The housing 40 may further be used as a return electrode alone or in combination with one or more of the coil electrodes, 28, 36, and 38 for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal $A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing, and shocking the connector also includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are configured for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design of the microcontroller 60 are not critical to the present invention. Rather, any suitable microcontroller 60 can be used to carry out the functions described herein. The use of microprocessor-based control circuits for performing timing and data analysis functions are well known in the art. In specific embodiment of the present invention, the microcontroller 60 performs some or all of the steps associated with determining optimal pacing parameters in accordance with the present invention.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 1B, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

The switch bank-74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. Such sensing circuits, 82 and 84, can be used to determine cardiac performance values used in the present invention.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, in the appropriate chambers of the heart. The sensing circuits, 82 and 84, in turn, receive control signals over signal lines, 86 and 88, from the microcontroller 60 for purposes of measuring cardiac performance at appropriate times, and for controlling the gain, threshold, polarization charge removal circuitry (not shown), and timing of any blocking circuitry (not shown) coupled to the inputs of the sensing circuits, 82 and 86.

For arrhythmia detection, the device 10 utilizes the atrial and ventricular sensing circuits, 82 and 84, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to an external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

In the preferred embodiment, the stimulation device 10 further includes a physiologic sensor 108, that can be used to detect changes in cardiac performance or changes in the physiological condition of the heart. Accordingly, the microcontroller 60 can respond by adjusting the various pacing parameters (such as rate, AV Delay, RV-LV Delay, V-V Delay, etc.) in accordance with the embodiments of the present invention. The microcontroller 60 controls adjustments of pacing parameters by, for example, controlling the stimulation pulses generated by the atrial and ventricular pulse generators, 70 and 72. While shown as being included within the ICD 10, it is to be understood that the physiologic sensor 108 may also be external to the stimulation device 10, yet still be implanted within or carried by the patient. More specifically, the sensor 108 can be located inside the device 10, on the surface of the device 10, in a header of the device 10, or on a lead (which can be placed inside or outside the bloodstream).

The stimulation device 10 additionally includes a battery 110 which provides operating power to all of the circuits shown in FIG. 1B. For the ICD 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 1B, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown only for completeness.

In the case where the stimulation device 10 is intended to operate as an ICD, it must detect the occurrence of an arrhythmia, and automatically apply an appropriate pacing therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized to be recognize), and pertaining exclusively to the treatment of fibrillation. Accordingly, the microcontroller 60 is capable of controlling the synchronous or asynchronous delivery of the shocking pulses.

A feature of the present invention is the prevention of the immediate reinitiation of atrial fibrillation following cardioversion or pacing therapy. This feature is implemented in the instant embodiment with the delivery of pacing pulses, or stimuli, at multiple sites in the atria following an initial delivery of electrical therapy to terminate atrial fibrillation. As stated above, cardioversion is one type of electrical therapy used to terminate atrial fibrillation.

In the exemplary embodiment of FIG. 1B, pacing stimuli is delivered at multiple sites within a single atrium substantially synchronous with a first post-shock activation. That is, the pacing stimuli is delivered within about 1–5 microseconds of the post-shock activation. Multi-site pacing triggered by a sensed atrial activation will decrease the dispersion of activation in the atria, and therefor reduce the likelihood of focal or reentrant activation. As known in the art, focal activation is a spontaneous activation of the myocardium, or Purkinje fibers, that arises outside of the normal conduction pathways of the heart. It is though to be more likely to occur it there is a long pause between normal sinus beats. If the first activation is a focal activation following cardioversion, for example, then multi-site pacing triggered by that activation will decrease the conduction dispersion and the likelihood of reentry.

Similarly, if the first activation is a normal sinus beat but certain areas of the atria have remodeled faster than others, creating a conduction velocity dispersion, the multi-site pacing will activate the whole atria faster, blocking possible reentry. Therefore, the preferred embodiment of the present invention provides multiple-site pacing therapy within a single atrium to reduce the likelihood of reentry. In the preferred embodiment, the multi-site pacing locations include at least one left atrial epicardial electrode location and at least one right atrial septal location. This pacing therapy can be delivered using leads clinically available in a standard dual chamber defibrillation device.

Figure 2:
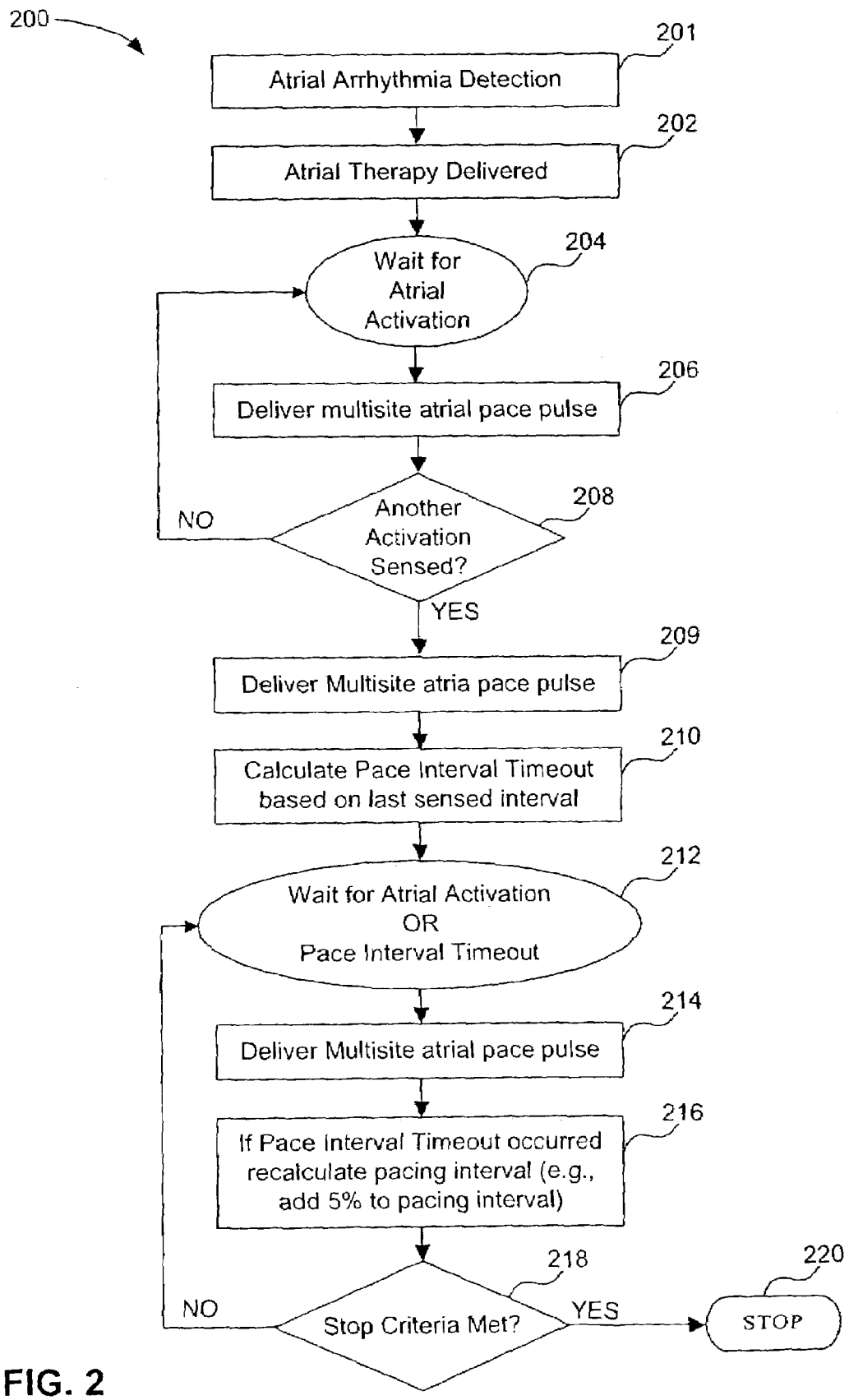
FIG. 2 is a flowchart illustrating an exemplary method of delivering pacing stimuli to the heart in accordance with the present invention.

FIG. 2 is a flowchart illustrating an exemplary method 200 of delivering pacing stimuli to the heart 12 in accordance with the present invention. In FIG. 2, the ICD 10 is configured to monitor the sinus rhythms of the heart 12. More specifically, the sensing circuits 82 and 84 are configured to detect an atrial arrhythmia as shown in block 201 of FIG. 2. Once the atrial arrhythmia has been detected, the shocking circuit 116, as instructed by the microprocessor controller 60, delivers atrial therapy electrical energy to the heart as depicted in block 202. The electrical energy provides a level of shock therapy to the heart 12 in order to terminate the atrial fibrillation.

After delivery of the shock therapy, the sensing circuits 82 and 84 search for the presence of a natural atrial activation within at least one of the left or right atrium. The sensing circuits 82 and 84 accomplish this by monitoring the connection leads 24, 20, and 30 as described in block 204 of FIG. 2. When an atrial activation is detected, a pacing pulse is delivered from the atrial pulse generator 70 to multiple sites within the atrium as described in block 206. This process is illustrated more clearly in the timing diagram shown in FIG. 3.

Figure 3:
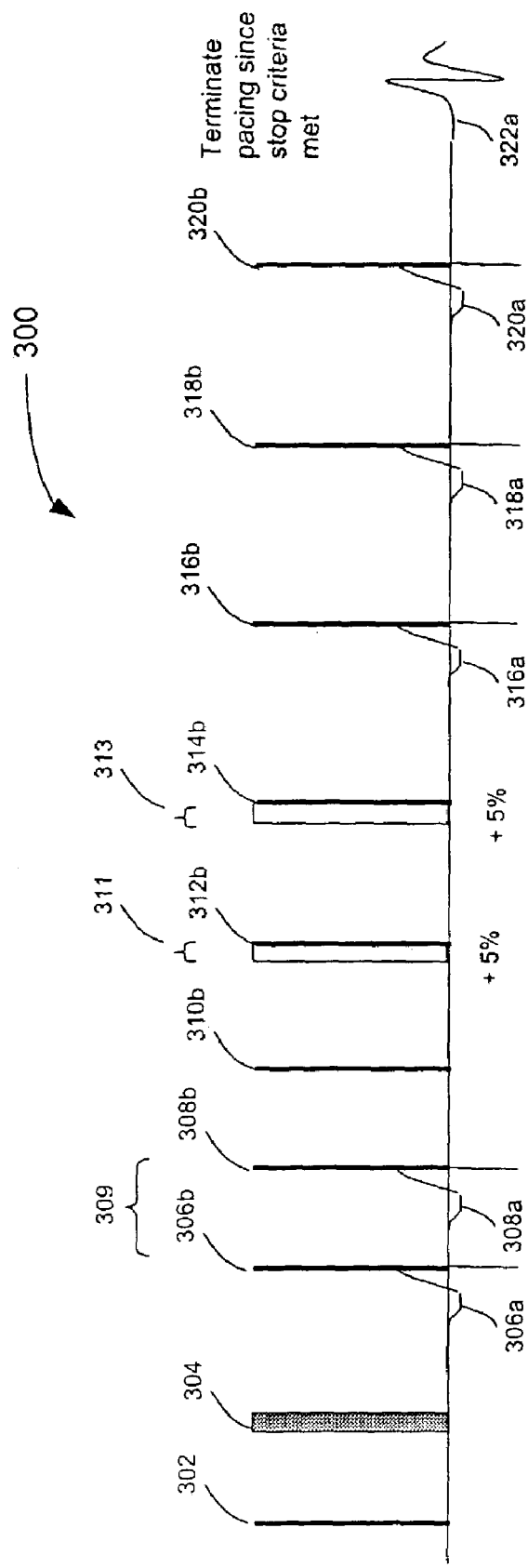
FIG. 3 is an exemplary timing diagram illustrating pacing pulses delivered in accordance with the present invention superimposed over an atrial signal.

In FIG. 3, a timing sequence 300 includes a number of pulses of varying amplitudes and spaced along a timing line. In FIG. 3, for example, a pulse 302 represents the presence of an atrial arrhythmia corresponding to block 201 of FIG. 2. Upon detection of the pulse 302, a therapeutic electrical shock pulse 304 is provided by the shocking circuit 116, as shown in block 202 of FIG. 2. After delivery of the pulse 304, the sensing circuits 82 and 84 search for the presence of a natural atrial activation, or beat, of the heart 12. This natural atrial activation is represented in FIG. 3 by a pulse 306a, also known as a sense event, depicted in block 204. Next, and in accordance with block 206 of FIG. 2, a pacing pulse 306b, also called a pacing event, is delivered substantially synchronous with the occurrence of the pulse 306a. In FIG. 3, the pacing event 306b is shown superimposed with the sense event 306a.

Referring back to FIG. 2, the sensing circuits 82 and 84 will now search to detect a second atrial activation, as depicted in block 208. When the second atrial activation is sensed, as indicated by the presence of sensing event 308a of FIG. 3, another pacing pulse 308b is delivered substantially synchronous with the sensing event 308a, as depicted in block 209 of FIG. 2.

In block 210 of FIG. 2, after delivery of the second pacing pulse 308b, the timing mechanism 79 calculates a pace interval timeout period based upon a timing interval 309 defined by an amount of time between the sense interval pulses 306a and 308a. The timing interval 309 is shown in FIG. 3. Next, the sensing circuits 82 and 84 detect expiration of the interval timeout period, as depicted in block 212 of FIG. 2. Substantially synchronous with the occurrence of the interval timeout period, a pacing pulse 310b is delivered, as shown in FIG. 3 and depicted in block 214 of FIG. 2.

If the interval timeout period occurred first, then the pace interval is recalculated, and an amount 311, equivalent to about 5% of the time of the timing interval 309, is added to the timeout period, as depicted in block 216. A pacing pulse 312b is then delivered at the end of the recalculated pacing timing interval, as shown in FIG. 3. If a natural atrial activation is still not detected, an additional amount 313, equivalent to 5%, is added to the timing interval and a pacing pulse 314b is delivered at the end of the interval. Although an amount of time equal to about 5% is suggested, a range of about 1 to 10% is suitable as depicted with 311b and 312b.

Finally, if predetermined stop criteria have been met, as depicted in block 218 of FIG. 2, a stop operation 220 is invoked. The predetermined pacing criteria can be, for example, the requirement that a particular number of sensing pulses be detected, as shown in FIG. 3 depicting sense events 316a, 318a, 320a, and 322a as stop criteria. Correspondingly, respective pacing pulses 316b, 318b, and 320b are delivered substantially synchronous with sense events 316a, 318a, and 320a. After occurrence of the predetermined stop criteria and occurrence of a final sense event 322a, the process ends.

On the other hand, if the predetermined pacing criteria 218 are not met, the microprocessor controller 60 returns to the detection block 212 to again wait for a naturally-occurring atrial activation or occurrence of another pace interval timeout period. Although FIG. 2 depicts calculation of a pace interval timeout period, the timeout period can be based on a previously-stored expected sinus rhythm, thus precluding the need to perform the calculation.

Figure 4A:
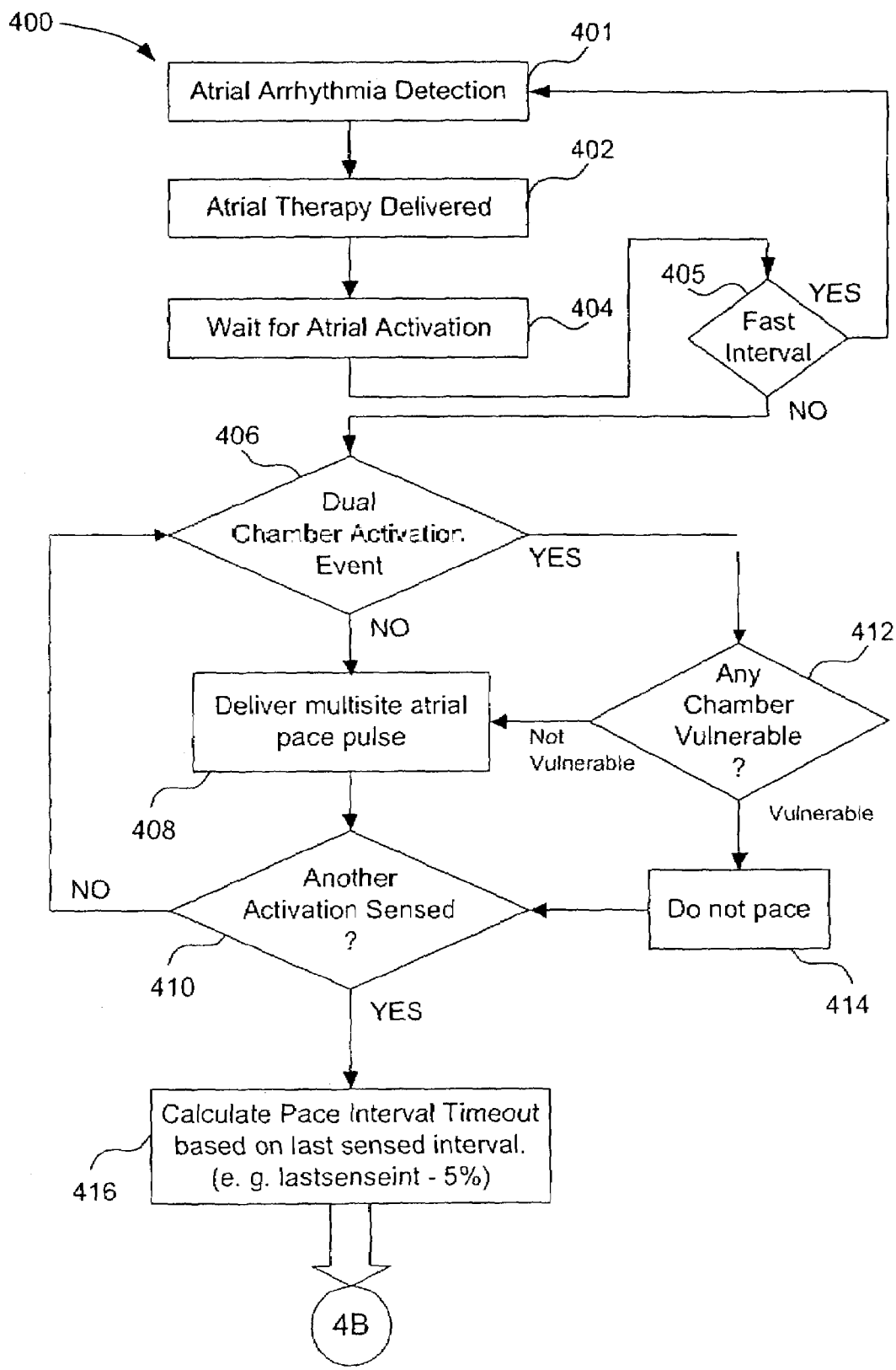
FIG. 4A is a flowchart of an alternative method of delivering pacing stimuli in accordance with the present invention.
Figure 4B:
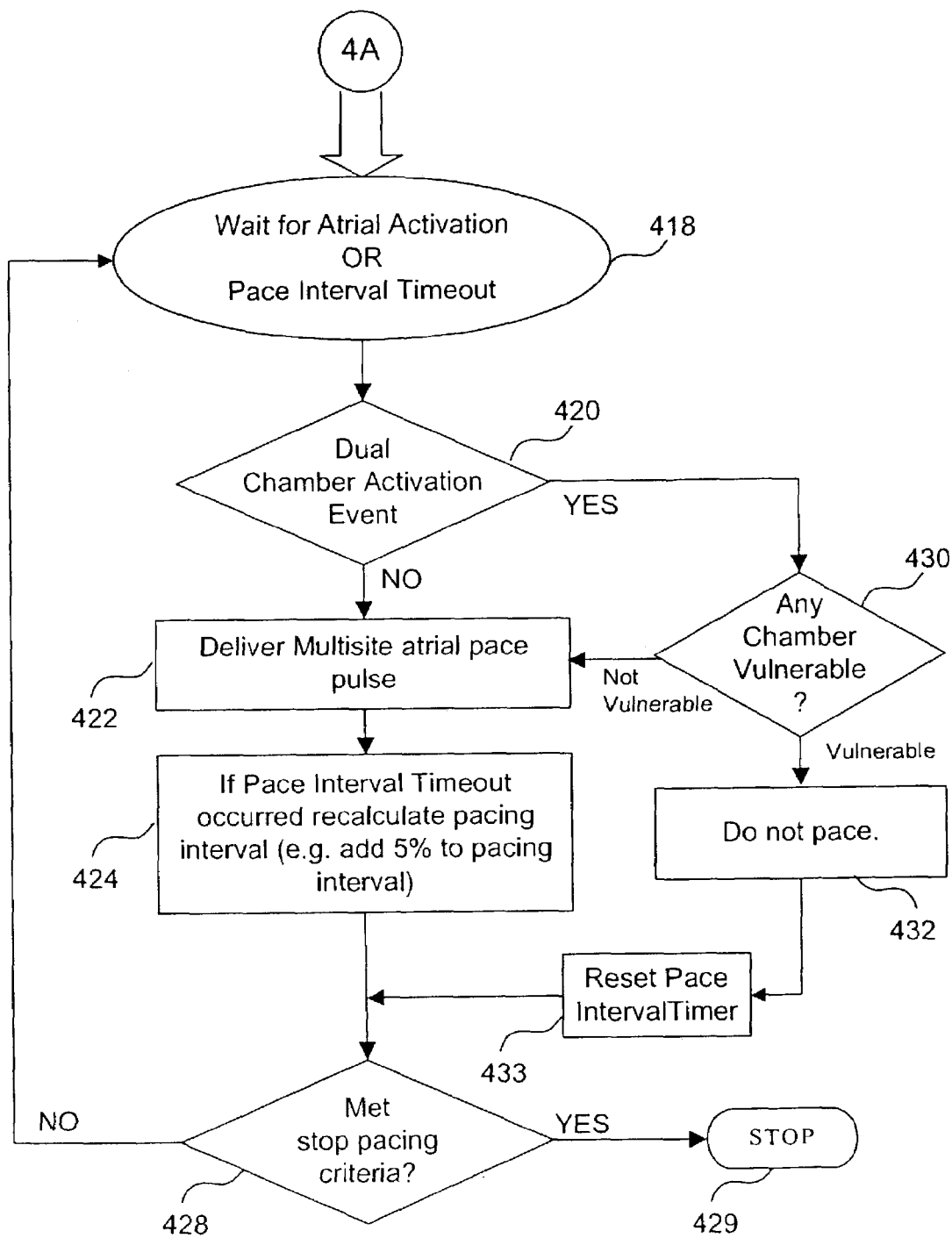
FIG. 4B is a continuation of the flow chart shown in FIG. 4A.

FIGS. 4A and 4B are flowcharts depicting an alternative method 400 of delivering pacing stimuli to the heart in accordance with the present invention. In the alternative method 400, bi-atrial sensing, also known as dual chamber sensing, is used to detect the sense events. Dual chamber sensing-provides additional guarantees for preventing the delivery of pacing stimulus during the heart's vulnerable period, that is, before completion of re-polarization. The alternative embodiment of FIG. 4 provides an additional step, accomplished by the microprocessor controller 60 and the sensing circuits 82 and 84, to determine if the heart is still within this vulnerable period.

In FIG. 4A, an atrial arrhythmia is detected in block 401 and therapeutic electrical energy is delivered in response to the detected atrial arrhythmia, as depicted in block 402. Also in FIG. 4A, as in the case of FIG. 2, a search is conducted for a naturally-occurring sense event by the sensing circuits 82 and 84, as depicted in block 404. In block 405, the microprocessor controller 60 determines if the detected sense event includes a fast interval. Interval timing, such as fast intervals, can be measured based upon predetermined atrial fibrillation rate criteria stored within the memory 94.

In FIG. 4A, the microprocessor controller 60 also determines whether sensing and/or pacing is being conducted within both chambers of the atria, as depicted in block 406. If, for example, the defibrillator is not configured for dual-chamber pacing, then a pacing pulse will be delivered to the multiple locations within the atria, as depicted in block 408 and in a manner similar to the embodiment of FIG. 2. After delivery of the pacing pulse, another search is conducted by the sensing circuits 82 and 84 to detect the presence of another atrial activation pulse, as shown in block 410.

If, however, the ICD 10 is configured for dual-chamber sensing and pacing, as determined in the block 406 of the method 400, then the microprocessor controller 60 determines whether any of the cardiac chambers are in a vulnerable state, as depicted in block 412. As stated above, the idea is to prevent delivery of pacing stimuli during the vulnerable period, which will typically increase the chance of ERAF. Therefore, if any of the atrial chambers is in the vulnerable state, a pacing pulse is not delivered, as depicted in block 414. That is, if either the left or right atria is in the vulnerable state, a pacing pulse is not delivered, and the device 10 continues to search for a second naturally-occurring activation pulse, as indicated in the block 410.

Next, as depicted in block 416, the pace interval timeout period is calculated as described above with reference to block 216 of FIG. 2. Afterwards, the microprocessor controller 60, via the sensing circuits 82 and 84, senses for another naturally-occurring atrial sense pulse or occurrence of a pace interval timeout, as depicted in block 418. Upon occurrence of the first of these, a determination is made whether dual-chamber sensing is used, as depicted in block 420. If the event depicted in block 418 is not a dual-chamber event, then another, multi-site atrial pacing pulse is delivered to the atria by the shocking circuit 116, as depicted in block 422. After delivery of the multi-site pacing pulse, the timeout interval is recalculated as indicated in block 424 in a manner similar to the discussion of block 216 of FIG. 2 above. Next, a determination is made as to whether the predetermined stop pacing criteria have been met, as depicted in block 428. If the stop pacing criteria have not been met, the process reverts back to the block 418. On the other hand, however, if the stop pacing criteria have been met, a stop operation is invoked at block 429.

If the determination made in block 420 was that a dual chamber activation event was sensed, then the microprocessor controller 60 will check to determine if any of the chambers is vulnerable, as depicted in block 430. Note, however, if a dual-chamber configuration is being used in block 420 in response to a pace-interval timeout that occurred in block 418, as opposed to occurrence of a sense event, then the microprocessor controller 60 will assume that none of the chambers is vulnerable. If, on the other hand, a vulnerable state is detected, a pacing pulse will not be delivered, as denoted in block 432. Afterwards, the pace interval timer is reset, as indicated in block 433, and a determination is made as to whether the criteria have been met as indicated in block 428.

By providing pacing therapy that includes delivery of pacing stimuli at multiple sites in the atria immediately synchronous with the first post-activation shock, ERAF following atrial therapy can be prevented. Multi-site pacing applied in accordance with the teachings of the present invention also decreases the delay in the activation of the atria, so that the chance of reentry path or focal activation taking over following atrial therapy is minimized. In the present invention, pacing leads are placed in both chambers of the atria, in order to provide the multi-site pacing. The technique of the present invention lowers the ADFT without creating further discomfort for the patient.

The foregoing description of the preferred embodiments provide an illustration and description, but is not intended to be exhaustive or to limit the invention to the precise form disclosed. Modifications and variations are possible consistent with the above teachings, or may be acquired from practice of the invention.

What is claimed is:

1. A method of applying electrical therapy to a human heart to prevent early return to atrial fibrillation (ERAF), the method comprising:
   detecting an atrial fibrillation;
   delivering electrical energy to at least one atrium in response to the detected atrial arrhythmia fibrillation to terminate the atrial fibrillation;
   monitoring for occurrence of a first atrial activation after delivering the electrical energy and after termination of the atrial fibrillation, occurrence of the detected first atrial activation defining a first moment; and
   delivering a first pacing pulse to a plurality of locations within the atria when the first atrial activation is detected, wherein the first pacing pulse is delivered at a second moment, the first and second moments being substantially synchronous.

2. The method of claim 1, further comprising:
   monitoring for occurrence of a second atrial activation after the second moment, occurrence of the detected second atrial activation defining a third moment; and delivering a second pacing pulse to the plurality of locations within the atria when the second atrial activation is detected, wherein the second pacing pulse is delivered at a fourth moment, the third and fourth moments being substantially synchronous.

3. The method of claim 2, further comprising:

calculating a time lapse value when the second atrial activation is detected, the time lapse value being representative of an interval of time between the first and third moments;

monitoring for occurrence of a third atrial activation for a period of time less than or equal to the time lapse value, wherein occurrence of a detected third atrial activation defines a fifth moment; and delivering a third pacing pulse to the plurality of locations within the atria when the third atrial activation is detected within the period of time, wherein the third pacing pulse is delivered at a sixth moment, the fifth and sixth moments being substantially synchronous.

4. The method of claim 3, further comprising delivering the third pacing pulse to the plurality of locations within the atria immediately after the period of time when the third atrial activation is not detected therewithin.

5. The method of claim 4, further comprising (i) applying a predetermined stop criteria and (ii) terminating the electrical therapy when the predetermined stop criteria has been met.

6. The method of claim 5, wherein the predetermined stop criteria includes detecting a plurality of consecutive atrial activations after the period of time.

7. The method of claim 6, further comprising performing at least a first adjustment to the time lapse value after delivering the third pacing pulse.

8. The method of claim 7, wherein the first adjustment includes increasing the time lapse value by a predetermined amount.

9. The method of claim 8, wherein the predetermined amount is within a range of about one to ten percent.

10. The method of claim 9, wherein the plurality of locations includes at least one left atrial epicardial location and one right atrial septal location.

11. The method of claim 1, wherein the electrical energy is cardioverting.

12. The method of claim 1, wherein the first atrial activation is a focal activation.

13. The method of claim 1, wherein the first atrial activation is a normal sinus beat.

14. The method of claim 1, wherein the first and second moments are within about 1–5 microseconds.

15. A method of applying atrial therapy to a human heart, the method comprising:

detecting an atrial arrhythmia;

delivering electrical energy to at least one atrium in response to the detected atrial arrhythmia to terminate the atrial arrhythmia;

detecting a first atrial activation after delivering the electrical energy and after terminating the atrial arrhythmia, occurrence of the detected first atrial activation defining a first moment; and delivering a first pacing pulse to a plurality of locations within the atria when the first atrial activation is detected, wherein the first pacing pulse is delivered at a second moment, the first and second moments being substantially synchronous.

16. The method of claim 15, further comprising:

monitoring for occurrence of a second atrial activation for a period of time less than or equal to the expected sinus rate, wherein occurrence of a detected second atrial activation defines a third moment; and delivering a second pacing pulse to the plurality of locations within the atria when the second atrial activation is detected within an expected sinus rate, the expected sinus rate being stored in the memory, wherein the second pacing pulse is delivered at a fourth moment, the third and fourth moments being substantially synchronous.

17. The method of claim 16, further comprising:

monitoring for occurrence of a third atrial activation for a period of time less than or equal to the expected sinus rate, wherein occurrence of a detected third atrial activation defines a fifth moment; and delivering a third pacing pulse to the plurality of locations within the atria when the third activation is detected within the expected sinus rate, wherein the second pulse is delivered at a sixth moment, the fifth and sixth moments being substantially synchronous.

18. The method of claim 17, further comprising delivering the third pulse to the plurality of locations within the atria immediately after the period of time when the third atrial activation is not detected therewithin.

19. The method of claim 18, wherein the plurality of locations includes at least one left atrial epicardial location and one right atrial septal location.

20. The method of claim 15, wherein the electrical energy is cardioverting.

21. A method of applying atrial therapy to a human heart using a defibrillator to prevent early return to atrial fibrillation (ERAF), the method comprising:

detecting an atrial arrhythmia fibrillation;

delivering electrical energy to at least one atrium in response to a detected atrial fibrillation to terminate the atrial fibrillation;

detecting a first atrial activation within a number of sense channels after delivering the electrical energy and after termination of the atrial fibrillation, occurrence of the detected first atrial activation defining a first moment;

performing a first determination of whether the number of sense channels indicates the heart is in a vulnerable state; and if the number of sense channels indicates the heart is not in a vulnerable state based upon the first determination, delivering a first pacing pulse to a plurality of locations within the atria at a second moment, the first and second moments being substantially synchronous.

22. The method of claim 21, further comprising:

detecting a second atrial activation after the second moment, occurrence of the detected second atrial activation defining a third moment;

delivering a second pacing pulse to the plurality of locations within the atria when the second atrial activation is detected, wherein the second pacing pulse is delivered at a fourth moment, the third and fourth moments being substantially synchronous; and calculating a time lapse value when the second atrial activation is detected, the time lapse value being representative of an interval of time between the first and third moments.

23. The method of claim 22, further comprising:

monitoring for occurrence of a third atrial activation for a period of time less than or equal to the time lapse value, wherein occurrence of a detected third atrial activation defines a fifth moment; and delivering a third pacing pulse to the plurality of locations within the atria when the third atrial activation is detected within the period of time, wherein the third pacing pulse is delivered at a sixth moment, the fifth and sixth moments being substantially synchronous.

24. The method of claim 23, further comprising delivering the third pacing pulse to the plurality of locations within the atria immediately after the period of time when the third atrial activation is not detected therewithin.

25. The method of claim 24, further comprising (i) applying a predetermined stop criteria and (ii) terminating the atrial therapy when the predetermined stop criteria has been met.

26. The method of claim 25, wherein the predetermined stop criteria includes detecting a plurality of consecutive atrial activations after the period of time.

27. The method of claim 26, further comprising performing at least a first adjustment to the time lapse value after delivering the third pacing pulse.

28. The method of claim 27, wherein the first adjustment includes increasing the time lapse value by a predetermined amount.

29. The method of claim 28, wherein the predetermined amount is within a range of about one to ten percent.

30. The method of claim 29, wherein the plurality of locations includes at least one left atrial epicardial location and one right atrial septal location.

31. The method of claim 21, further comprising detecting a second atrial activation when the number of sense channels is in a vulnerable state, occurrence of the second atrial activation defining the second moment;
calculating a time lapse value when the second atrial activation is detected, the time lapse value being representative of an interval of time between the first and second moments; and
monitoring for occurrence of a third atrial activation for a period of time less than or equal to the time lapse value, wherein occurrence of a detected third atrial activation defines a third moment; and
performing at least a second determination of whether the number of sense channels is in a vulnerable state.

32. The method of claim 31, further comprising delivering a third pacing pulse to the plurality of locations within the atria at a third moment if the number of sense channels is not in a vulnerable state based upon the second determination, the first and third moments being substantially synchronous.

33. The method of claim 32, further comprising performing at least a first adjustment to the time lapse value after delivering the first pacing pulse.

34. The method of claim 33, wherein the first adjustment includes increasing the time lapse value by a predetermined amount.

35. The method of claim 34, wherein the predetermined amount is within a range of about one to ten percent.

36. The method of claim 35, wherein the plurality of locations includes at least one left atrial epicardial location and one right atrial septal location.

37. The method of claim 21, wherein the electrical energy is cardioverting.

38. A computer readable medium carrying one or more sequences of one or more instructions for execution by one or more processors, the instructions when executed by the one or more processors, cause the one or more processors to perform the steps of:
detecting an atrial fibrillation within an atrium of a human heart;
delivering electrical energy to at least one atria in response to the detected atrial fibrillation;
detecting a first atrial activation after delivering the electrical energy and after terminating the atrial fibrillation, occurrence of the detected first atrial activation defining a first moment; and
delivering a first pacing pulse to a plurality of locations within the atria when the first atrial activation is detected, wherein the first pacing pulse is delivered at a second moment, the first and second moments being substantially synchronous.

39. The computer readable medium of claim 38, carrying the one or more instructions, further causing the one or more processors to:
detect a second atrial activation after the second moment, occurrence of the detected second atrial activation defining a third moment;
deliver a second pacing pulse to the plurality of locations within the atria when the second atrial activation is detected, wherein the second pacing pulse is delivered at a fourth moment, the third and fourth moments being substantially synchronous; and
calculate a time lapse value when the second atrial activation is detected, the time lapse value being representative of an interval of time between the first and third moments.

40. The computer readable medium of claim 39, carrying the one or more instructions, further causing the one or more processors to:
monitor for occurrence of a third atrial activation for a period of time less than or equal to the time lapse value, wherein occurrence of a detected third atrial activation defines a fifth moment; and
deliver a third pacing pulse to the plurality of locations within the atria when the third atrial activation is detected within the period of time, wherein the third pacing pulse is delivered at a sixth moment, the fifth and sixth moments being substantially synchronous.

41. The computer readable medium of claim 40, carrying the one or more instructions, further causing the one or more processors to deliver the third pacing pulse to the plurality of locations within the atria immediately after the period of time when the third atrial activation is not detected therewithin.

42. The computer readable medium of claim 41, further causing the one or more processors to (i) apply a predetermined stop criteria and (ii) terminate the delivering of electrical energy when the predetermined stop criteria has been met.

43. The computer readable medium of claim 42, wherein the predetermined stop criteria includes detecting a plurality of consecutive atrial activations after the period of time.

44. The computer readable medium of claim 43, carrying the one or more instructions, further causing the one or more processors to perform at least a first adjustment to the time lapse value after delivering the second pacing pulse.

45. The computer readable medium of claim 44, wherein the adjustment includes increasing the time lapse value by a predetermined amount.

46. The computer readable medium of claim 38, wherein the electrical energy is cardioverting.

47. An apparatus to prevent early return to atrial fibrillation (ERAF) comprising;
means for detecting an atrial fibrillation;
means for delivering electrical energy to at least one atrium in response to the detected atrial fibrillation;
means for detecting a first atrial activation after delivering the electrical energy and after terminating the atrial fibrillation, occurrence of the detected first atrial activation defining a first moment; and means for delivering a first pacing pulse to a plurality of locations within the atria when the first atrial activation is detected, wherein the first pacing pulse is delivered at a second moment, the first and second moments being substantially synchronous.

48. The apparatus of claim 47, further comprising:

means for detecting a second atrial activation after the second moment, occurrence of the detected second atrial activation defining a third moment;

means for delivering a second pacing pulse to the plurality of locations within the atria when the second atrial activation is detected, wherein the second pacing pulse is delivered at a fourth moment, the third and fourth moments being substantially synchronous; and means for calculating a time lapse value when the second atrial activation is detected, the time lapse value being representative of an interval of time between the first and third moments.

49. The apparatus of claim 48, further comprising:

means for monitoring for occurrence of a third atrial activation for a period of time less than or equal to the time lapse value, wherein occurrence of a detected third atrial activation defines a fifth moment; and means for delivering a third pacing pulse to the plurality of locations within the atria when the third atrial activation is detected within the period of time, wherein the third pacing pulse is delivered at a sixth moment, the fifth and sixth moments being substantially synchronous.

50. The apparatus of claim 49, further comprising means for delivering the third pacing pulse to the plurality of locations within the atria immediately after the period of time when the third atrial activation is not detected therewithin.

51. The apparatus of claim 50, further comprising means for (i) applying a predetermined stop criteria and (ii) terminating delivering the electrical energy when the predetermined stop criteria has been met.

52. The apparatus of claim 51, wherein the predetermined stop criteria includes detecting a plurality of consecutive atrial activations after the period of time.

53. The apparatus of claim 52, further comprising means for performing at least a first adjustment to the time lapse value after delivering the second pacing pulse.

54. The apparatus of claim 53, wherein the first adjustment includes increasing the time lapse value by a predetermined amount.

55. The apparatus of claim 47, wherein the electrical energy is cardioverting.

56. An apparatus comprising:

(a) a detector configured to (i) detect a first atrial activation within at least one atrium of a human heart at a first moment following termination of an atrial arrhythmia and (ii) produce an activation detection signal representative of the detected atrial activation;

(b) a processor electrically connectable to the detector and configured to (i) receive the activation detection signal and (ii) produce a post-activation signal responsive to the activation detection signal; and (c) a pulse generator electrically connectable to the processor and configured to (i) receive the post-activation signal, (ii) produce a pacing pulse in response to the received post-activation signal, and (iii) deliver the pacing pulse to a plurality of locations within the atria at a second moment, the first and second moments being substantially synchronous.

57. The apparatus of claim 56, wherein the detector is configured to detect a second atrial activation after the second moment, occurrence of the detected second atrial activation defining a third moment;

wherein the pulse generator delivers a second pacing pulse to the plurality of locations within the atria when the second atrial activation is detected, the second pacing pulse being delivered at a fourth moment; and wherein the third and fourth moments are substantially synchronous.

58. The apparatus of claim 56, further comprising a calculator configured to calculate a time lapse value when the second atrial activation is detected, the time lapse value being representative of an interval of time between the first and third moments;

wherein (i) the detector is configured to detect a third atrial activation, (ii) the detecting of the third atrial activation is performed for a period of time less than or equal to the time lapse value, and (iii) occurrence of the detected third atrial activation defines a fifth moment;

wherein (i) the pulse generator delivers a third pacing pulse to the plurality of locations within the atria when the third atrial activation is detected within the period of time, (ii) the third pacing pulse is delivered at a sixth moment, and (iii) the fifth and sixth moments are substantially synchronous; and wherein the pulse generator delivers the third pacing pulse to the plurality of locations within the atria immediately after the period of time when the third atrial activation is not detected therewithin.

59. The apparatus of claim 58, wherein the plurality of locations includes at least one left atrial epicardial location and one right atrial septal location.

60. The apparatus of claim 58, further comprising a terminating device configured to terminate delivery of the pacing pulses in accordance with a predetermined stop criteria.

61. The apparatus of claim 60, wherein the predetermined stop criteria includes detecting a plurality of consecutive atrial activation after the period of time.

62. The apparatus of claim 56, wherein the first atrial activation is a focal activation.

63. The apparatus of claim 56, wherein the first atrial activation is a normal sinus beat.

64. The apparatus of claim 56, wherein the first atrial activation is detected after delivering a cardioversion to terminate atrial fibrillation.

65. The apparatus of claim 56, wherein the first and second moments are within about 1–5 microseconds.

* * * * *